(12) United States Patent
Glynn et al.

(10) Patent No.: US 10,168,217 B2
(45) Date of Patent: *Jan. 1, 2019

(54) AUTOMATED THERMOGRAPHIC INSPECTION FOR COMPOSITE STRUCTURES

(71) Applicant: Amazon Technologies, Inc., Seattle, WA (US)

(72) Inventors: Prescott Gee Glynn, Sammamish, WA (US); Robert Todd Marks, Seattle, WA (US); Steven McGinnis, Seattle, WA (US); Armando Medina Romero, Lynnwood, WA (US); Mark Gerald Munster, Jr., Everett, WA (US); Adrian Timothy Wallace, Seattle, WA (US)

(73) Assignee: Amazon Technologies, Inc., Seattle, WA (US)

( * ) Notice: Subject to any disclaimer, the term of this patent is extended or adjusted under 35 U.S.C. 154(b) by 121 days.

This patent is subject to a terminal disclaimer.

(21) Appl. No.: 15/279,078

(22) Filed: Sep. 28, 2016

(65) Prior Publication Data

US 2018/0087967 A1    Mar. 29, 2018

(51) Int. Cl.
*G01N 25/72* (2006.01)
*G01J 5/00* (2006.01)
*G01J 5/08* (2006.01)

(52) U.S. Cl.
CPC .......... *G01J 5/0003* (2013.01); *G01J 5/0896* (2013.01); *G01N 25/72* (2013.01); *G01J 2005/0077* (2013.01); *G01J 2005/0085* (2013.01)

(58) Field of Classification Search
None
See application file for complete search history.

(56) References Cited

U.S. PATENT DOCUMENTS

| | | |
|---|---|---|
| 2005/0186327 A1 | 8/2005 | Saito et al. |
| 2006/0191622 A1 | 8/2006 | Ritter et al. |
| 2012/0069174 A1 | 3/2012 | Ye et al. |
| 2012/0219034 A1 | 8/2012 | Nielsen |
| 2014/0022380 A1 | 1/2014 | Nissen et al. |
| 2014/0200731 A1* | 7/2014 | Evens ............... B29C 73/12 700/300 |
| 2015/0153293 A1* | 6/2015 | Nosrati ............... G01N 25/72 374/5 |

(Continued)

FOREIGN PATENT DOCUMENTS

| | | |
|---|---|---|
| EP | 0089760 | 9/1983 |
| JP | 08145922 | 6/1996 |

OTHER PUBLICATIONS

U.S. Appl. No. 15/279,027, U.S. Patent Application, filed Sep. 28, 2016, Titled: Thermographic Inspection Process for Composite Vehicle and Components.

(Continued)

*Primary Examiner* — Andre Allen
(74) *Attorney, Agent, or Firm* — Kilpatrick Townsend & Stockton LLP

(57) ABSTRACT

Methods for detecting irregularities in a composite structure can include obtaining temperature data from a surface of the composite structure while the composite structure undergoes a thermal change. An irregularity in the composite structure is detected based on the temperature data.

20 Claims, 18 Drawing Sheets

(56) References Cited

U.S. PATENT DOCUMENTS

2018/0087967 A1* 3/2018 Glynn .................. G01J 5/0003
2018/0088063 A1* 3/2018 Glynn .................... G01N 25/72
2018/0104742 A1* 4/2018 Kottilingam .......... B29C 64/393

OTHER PUBLICATIONS

D'Orazio et al., "Defect detection in aircraft composites by using a neural approach in the analysis of thermographic images", *NDT & E International*, vol. 38, Issue 8 (Dec. 2005), pp. 665-673.
PCT/US2017/053604, International Search Report and Written Opinion, dated Nov. 22, 2017, 14 pages.

* cited by examiner

AUTOMATED THERMOGRAPHIC INSPECTION FOR COMPOSITE STRUCTURES

CROSS-REFERENCES TO RELATED APPLICATIONS

This application is related to and incorporates by reference for all purposes the full disclosure of U.S. patent application Ser. No. 15/279,027, filed Sep. 28, 2016, entitled "THERMOGRAPHIC INSPECTION PROCESS FOR COMPOSITE VEHICLE AND COMPONENTS"; P34488-US).

BACKGROUND

Many personal, commercial, and industrial structures and devices are made from composite structures because composite structures can have high strength and/or stiffness at a low weight. One composite structure configuration, which is present in a variety of applications including unmanned aerial vehicles, includes a lightweight core (e.g., a foam core, balsa core, honeycomb aramid core, and the like) and an overlying composite skin, such as a carbon fiber laminate. The composite skin can include any suitable number of composite plies. Each of the composite plies typically includes composite fibers embedded in a matrix. The composite plies in the composite skin can be oriented to orient the composite fibers in suitable directions. Composite structure can be very strong and very light, but may also be susceptible to in-service damage (e.g., impact damage). In many instances, a damaged composite structure many not show obvious visible signs of damage. Additionally, in many instances, a composite structure many not show obvious visible signs of manufacturing defects (e.g., voids, delaminated areas, resin starved areas).

Because composite structures may not show obvious visible signs of damage and/or manufacturing defect, a variety of inspection methods have been employed to detect the damage and/or manufacturing defect. Common forms of damage include the development of voids, delamination or debond, buckling, and cracks in either (or both of) composite plies and/or composite core. Existing inspection methods include tap testing, ultrasound testing, and radiographic means. Tap testing can include systematic tapping a surface of a composite structure and searching for damage by listening for dead sounds or resonant sounds. Ultrasonic testing can include using an ultrasound scanner that emits ultrasonic pulses and processes resulting return ultrasonic pulses to detect faults in a composite skin or in a composite core. Existing composite inspection methods, however, may have drawbacks in terms of labor, materials (e.g., ultrasound gel) and the potential for operator error. Thus, improved inspection methods for detecting damage and/or manufacturing defects in composite structures are of interest.

BRIEF DESCRIPTION OF THE DRAWINGS

Various embodiments in accordance with the present disclosure will be described with reference to the drawings, in which.

DETAILED DESCRIPTION

Figure 1:
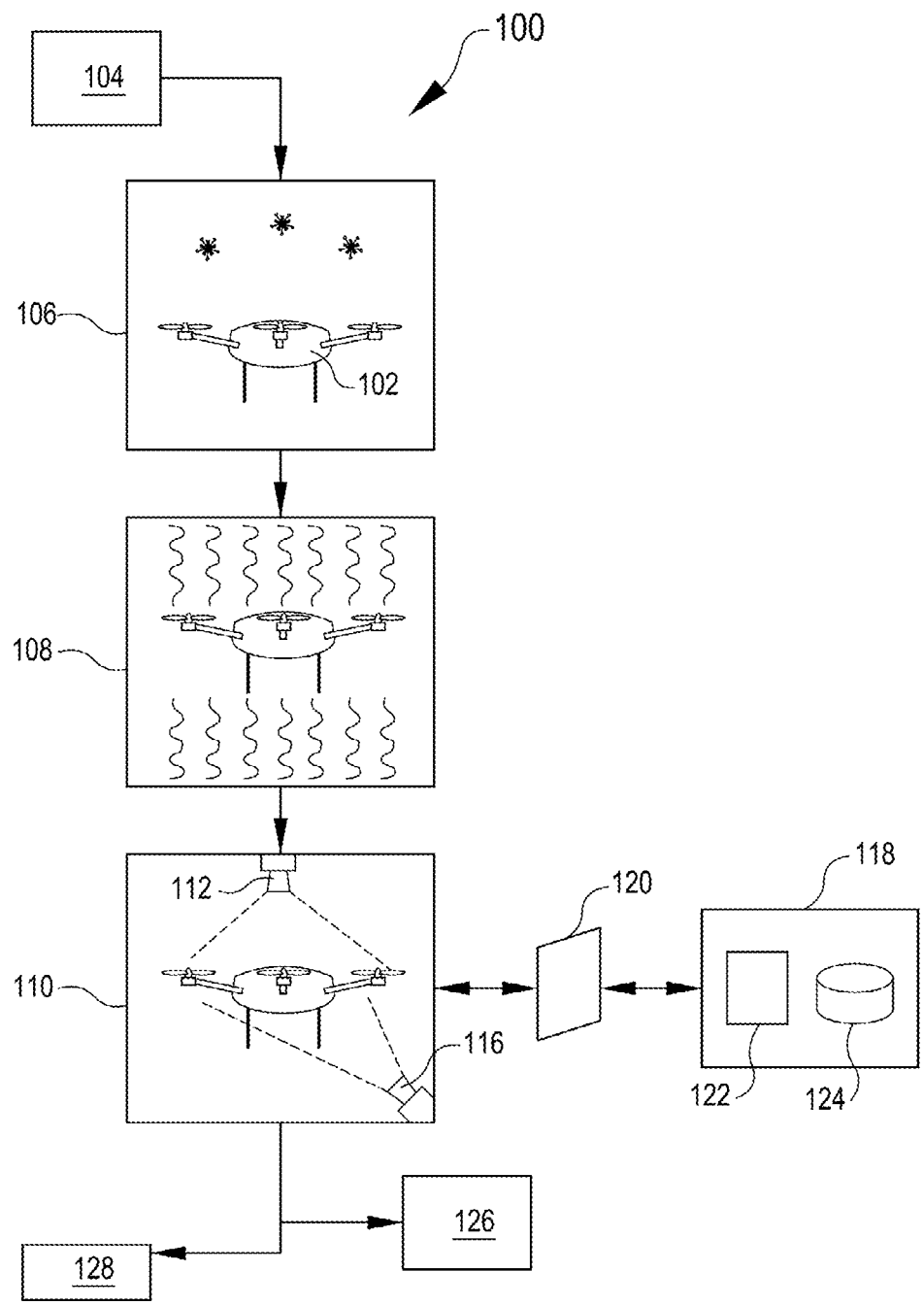
FIG. 1 illustrates a system for thermographically inspecting a composite structure of a vehicle, in accordance with embodiments.

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

Embodiments herein are directed to inspection systems and methods for identifying irregularities in a composite structure. Specifically, features herein are directed to systems and methods with a chilling mechanism operable to cool a composite vehicle or composite component, and particularly a composite component that has an outer layer and a substrate or core within the outer layer. A heating mechanism is operable to heat the outer layer of the composite component. A thermographic sensor, such as an infrared camera, is operable to obtain temperature data based on a temperature of the outer layer of the composite component. Systems can, by way of a management component, cause the chilling mechanism to cool the outer layer and the core of the composite component to a first temperature state. A first temperature state can refer to, e.g., a steady state temperature regime where the outer layer and core of the composite component are within a limited range of temperatures throughout, which can be less than an ambient temperature, and then cause the heating mechanism to heat the outer layer of the composite component to a transient temperature higher than the first steady state temperature, which can be greater than an ambient temperature. The systems can then cause the thermographic sensor to obtain temperature data from the composite component as the outer layer of the composite component cools from the transient temperature toward an ambient temperature. The core or substrate of the composite component, which is at a lower temperature than the outer layer, will draw heat away from the outer layer as the vehicle undergoes a thermal change toward equilibrium with the ambient temperature. The core or substrate draws heat from the outer layer at a nontrivial rate for outer layers comprising multi-ply composite skins having at least 14 individual layers or more. In some cases, the ambient temperature may be a room temperature, which may or may not be controlled. In some other cases, the ambient temperature may be a specific temperature subject to environmental control. For example, a suitable ambient temperature for thermographically inspecting a composite component can include 20-24° C. In some other cases, a suitable ambient temperature for thermographically inspecting a composite component may include 18-26° C., 16-28° C., or a wider range of temperatures. Generally, a suitable ambient temperature for thermographically inspecting composite component will be at least 11° C. less than a heated temperature of the outer layer of the component. In some cases, the suitable ambient temperature may be at least 30° C. less than the heated temperature, or in some cases, may be about 33° C. less than the heated temperature.

Many forms of structural irregularities can disrupt the thermal conductivity between the outer layer of the composite component and the substrate, such as but not limited to: voids, delamination or debond, buckling, and cracks. As the temperature of the composite structure equilibrates, such irregularities will appear in the thermographic data as "hot spots" or regions of local high intensity compared to the surrounding structure. Thus, many irregularities in the composite structure may be detected based on the temperature data.

In accordance with embodiments, systems for thermographically inspecting a composite part can also generate a thermographic image from the temperature data, and the thermographic image can be used to indicate temperatures of the outer layer of the composite vehicle, and thus be used to detect the irregularity. In some cases, the thermographic image can be compared to a reference image indicative of temperatures of the outer layer of the composite vehicle when the composite vehicle does not have irregularities. For example, in some cases, a composite vehicle can be scanned before service, and a reference image can be stored in a database for later use to assess whether a change in the structural integrity has occurred as a result of any service-related impact, damage, or wear and tear. A new thermographic image can be compared to the reference image; and any irregularities can be assessed based on differences between the images that exceed a predetermined threshold.

In some embodiments, a composite component is chilled to a first steady state temperature of approximately 16° C. or less, and then transiently heated to an outer surface temperature of approximately 43° C. or more. In general, a temperature difference between the first steady state temperature and the transient temperature of at least 33° C. is obtained; however, in some embodiments the temperature difference may be about 30° C., 25° C., 20° C., 15° C., 11° C., or less.

It will be understood that the methods for detecting irregularities may be performed in similar manner by inverting the order of heating and cooling. For example, a composite part may be uniformly heated to a steady state temperature throughout, and may then be subjected to cooling at an outer surface of the part that quickly lowers a temperature of an exposed layer of the part. The composite part may then be subjected to ambient temperatures that are higher than the cool temperature of the outer layer. A thermographic image of the composite part may be generated while the composite part is reverting to thermal equilibrium at the higher ambient temperature.

Sufficient resolution in the thermographic image may be obtained when the difference between the first, steady state temperature and the transitory temperature have at least a minimum delta. In examples described above, for methods and systems that begin with a cool initial steady-state temperature, employ a heated transitory temperature, and return to a cool ambient temperature, suitable deltas (i.e., difference between the hot temperature and the cold temperature) may range from about 11° C. to 33° C., or more. The minimum delta is driven in part by the sensitivity of available thermographic imaging technology. For sensors that are sensitive to temperature differences on the order of about 1-2° C., a minimum delta of about 11° C. is sufficient to capture irregularities a surface of a composite part by way of visualizing heat transfer in the part caused by the temperature change. As sensors improve, it is anticipated that a minimum delta to achieve the methods described herein will decrease to less than 11° C.

Similarly, for methods and systems that employ a hot initial steady-state temperature, employ a cooled transitory temperature, and return to a hot ambient temperature, suitable deltas may also range from about 11° C. to about 33° C., or more. Systems and methods that employ a hot initial, steady state temperature may be advantageous under conditions where it is more energy efficient to heat the composite part than to cool the part. It will be understood that the embodiments herein disclosed may employ cooling and heating steps in different orders than those described in order to facilitate the inverted order of heating and cooling.

Methods and systems herein described may apply to any suitable composite structure having an outer layer and a substrate or core. The outer layer can be any suitable composite skin, such as a laminate including one or more bonded composite layers (e.g., carbon fiber composite, fiberglass composite, polymer-polymer composite, fabric composite, or the like,) forming a composite skin, a resin or other polymer shell, or other suitable outer layer. The outer layer is directly connected with the substrate, which can be any suitable substrate including but not limited to: a foam core, a honeycomb structure formed of, e.g., aramid or other suitable polymer, a balsa core, or the like. The outer layer and substrate are preferably in thermal contact for at least a portion of the outer layer.

In some embodiments, systems and methods can include moving a composite structure or composite vehicle between stations that are configured to achieve the chilling, heating, and/or scanning steps. For example, a chilling mechanism can be provided at a chilling station, and the composite structure can be placed within the chilling station for a period of time that achieves the first steady-state temperature. The heating mechanism can likewise be provided at a heating station, so that the composite structure can be conveyed from one to the other, and so that the respective stations can retain their respective temperatures. However, in some cases, the mechanisms for chilling, heating, and/or scanning can also be co-located, e.g., one or more standalone systems that achieve an entire inspection cycle.

FIG. 1 illustrates a system 100 for thermographically inspecting a composite structure 102, in accordance with embodiments. The system 100 includes stations or stages through which the composite structure 102 can pass during an inspection procedure. The stages may refer to physical stations through which a composite structure is moved, or may refer to distinct processes that occur at a single location. Although a composite vehicle is used for illustrative purposes, and specifically a composite unmanned aerial vehicle (UAV), it will be understood that the principles described herein may apply to any comparably situated composite structure having an outer skin and a core.

The composite structure 102 is can be routed from a pre-inspection stage 104, which may include a receiving station, a manual inspection stage, or any comparable pre-inspection stage. For example, where the composite structure 102 is a UAV, the pre-inspection stage 104 may be a receiving pad where the UAV is directed to land after a predetermined number of flights, a predetermined number of service hours, after a physical impact, or any other suitable criteria.

In a first, or chilling stage 106, the composite structure 102 can be exposed to cold to reduce a temperature of the composite structure 102 to a predefined initial temperature, i.e., a first steady-state temperature. The chilling stage 106 may include any suitable means of cooling a structure, preferably quickly. In some cases, the cooling stage 106 may include a heat exchanger in an enclosed space, i.e., a conventional chiller or freezer. In some cases, the cooling stage 106 may provide convective heat transfer to more rapidly cool the composite structure 102. In some cases, the cooling stage 106 can include means to douse or submerging the composite structure in a cold fluid, such as an ice bath, a dry ice/methanol bath, or similar. In some embodiments, a composite structure is chilled to a first steady state temperature of approximately 16° C. or less. In some cases, the composite structure is chilled to a lower first steady-state temperature, e.g., about 10° C. or less, or as low as about −7° C.

In a second, heating stage 108, the composite structure 102 can be exposed to a heat source to quickly raise the temperature of an outer layer of the composite structure. Suitable heat sources may include a heat exchanger in an enclosed space (i.e., a conventional heater), which may include convective means to more rapidly distribute heat to the surface of the composite structure 102, such as a fan. Other suitable heat sources can include an infrared heat source, similar to a heat lamp. In some embodiments, the composite structure is heated until an outer surface reaches a temperature of at least 43° C., or more. In general, a temperature difference between the first steady state temperature and the transient temperature of at least 33° C. is obtained.

In a third, scanning stage 110, the composite structure 102 is permitted to begin coming to a thermal equilibrium, during which a cool interior (i.e., the composite core or substrate and/or an inner part of the composite skin) draws heat from the warm exterior. The scanning stage 110 can include any suitable number of thermal sensors 112, 116, such as infrared sensors (e.g., forward looking infrared (FLIR) cameras or scanners) operable to take a thermal image showing infrared emissions from an object. The scanning stage 100 shown illustrates thermal sensors 112, 116 positioned to capture temperature data in the form of thermographic images from a zenith and from a side view of the composite structure; however any suitable combination of image capture positions may be used. The scanning stage 110 can communicate data 120, including temperature data and instructions, between the thermal sensors 112, 116 and a management component 118 which includes a processor 122 and memory 124, and is operable to control operation of the system 100 including, but not limited to, timing and temperatures for each stage 106, 108, 110; temperature data capture by the thermal sensors 112, 116, and analysis of the temperature data captured thereby. If a composite structure is determined to be undamaged, i.e., without irregularities observed during the inspection, the management component 118 can cause the system to direct the composite structure (e.g., a UAV) to a first output station 128 associated with a passed inspection. In the case of a UAV, the first output station 128 might be an "in service" station or a launch station. If the composite structure is determined to have irregularities, the management component 118 can instead cause the system to direct the composite structure to a second output station 126 associated with a failed inspection, e.g., a holding station for further inspection or decommission.

As noted above, in some cases, the order of cooling a composite structure 102 and heating the composite structure may be reversed. In such cases, the positions of the heating stage 108 and the cooling stage 106 may be reversed. The scanning stage 110 may also be provided with mechanisms to heat or cool the composite structure 102, in order to control an ambient temperature, so that there is provided sufficient temperature delta to resolve changes in thermal conductivity of the composite structure. For example, in the embodiment shown (with cooling stage 106 preceding heating stage 108), the scanning stage 110 may include a secondary cooling mechanism to control and reduce the ambient temperature therein. In the inverse embodiments (with a cooling stage 106 after heating stage 108) the scanning stage 110 may instead include a secondary heating mechanism to control and increase the ambient temperature therein.

Figure 2:
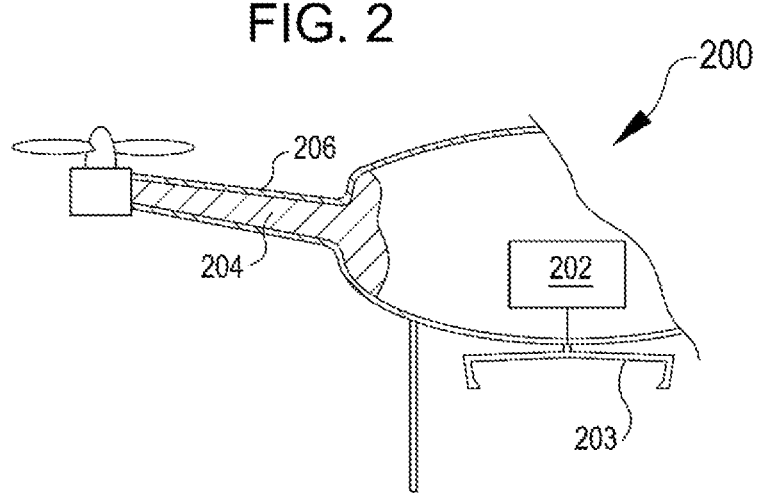
FIG. 2 illustrates an example of a reference composite structure, in a diagrammatic side-section view, without irregularities.

FIG. 2 illustrates an example of a composite structure 200, in a diagrammatic side-section view, shown as a reference composite vehicle without irregularities. FIGS. 3-7 illustrate some examples of irregularities that can be detected by way of thermographic systems and methods discussed herein.

The composite structure 200 may have operational elements 202, 203, such as internal components 202 and external components 203. In the example shown, the composite structure 200 is a UAV that contains internal electronics 202 and a grasper 203. It will be understood that the principles disclosed herein may readily apply to a wide variety of composite structures including various other vehicles, including autonomous vehicles that may have different operational elements.

The composite structure 200 includes an outer layer 206 that is connected with a substrate 204. The outer layer 206 can be any suitable composite skin, such as a laminate including one or more bonded composite layers (e.g., carbon fiber composite, fiberglass composite, polymer-polymer composite, fabric composite, or the like), a polymer shell, or other suitable outer layer 206. In embodiments, the outer layer 206 can be directly connected with the substrate 204, which can be any suitable substrate 204 including but not limited to: a foam core, a honeycomb structure formed of, e.g., aramid or other suitable polymer, a balsa core, or the like. The outer layer 206 and substrate 204 are preferably in thermal contact for at least a portion of the outer layer 206. In some cases, the outer layer 206 and substrate 204 are adhered together.

Figure 3:
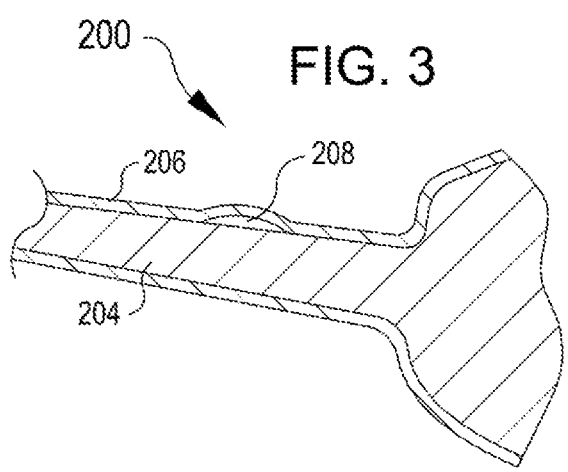
FIG. 3 illustrates the composite structure of FIG. 2, in a diagrammatic side-section view; showing a separation irregularity.

FIG. 3 illustrates the composite structure 200 of FIG. 2, in a diagrammatic side-section view; showing a separation irregularity 208. A separation irregularity can include any separation of the outer layer 206 from the substrate 204. For example, a composite skin can debond or delaminate from a core in a composite; a bubble can be formed between a composite skin and a core; or an impact to the composite structure 200 might intent the substrate 204 allowing a void to form between the substrate and the outer layer 206. The separation irregularity 208 can prevent direct thermal transfer between the substrate 204 and the outer layer 206.

Figure 4:
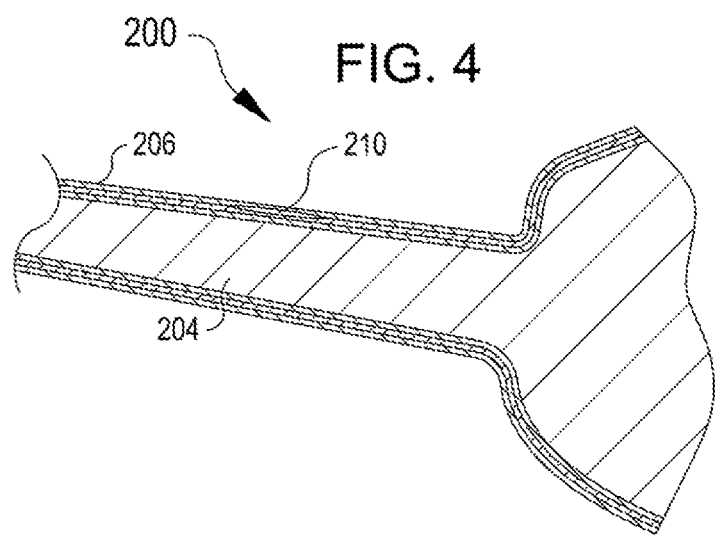
FIG. 4 illustrates the composite structure of FIG. 2, in a diagrammatic side section view, showing a delamination irregularity occurring within a multi-ply composite skin.

FIG. 4 illustrates the composite structure 200 of FIG. 2, in a diagrammatic side section view, showing a delamination irregularity 210 occurring within a multi-ply composite skin forming the outer layer 206. Delamination can occur whenever a matrix binding a multi-ply composite is damaged or degraded (e.g., by heat or impact) or when a matrix binding a composite is not fully impregnated into the composite layers (e.g., when an air bubble forms in the composite layers). The delamination can impair the strength of the composite. The delamination can interfere with thermal transfer through the outer layer 206.

Figure 5:
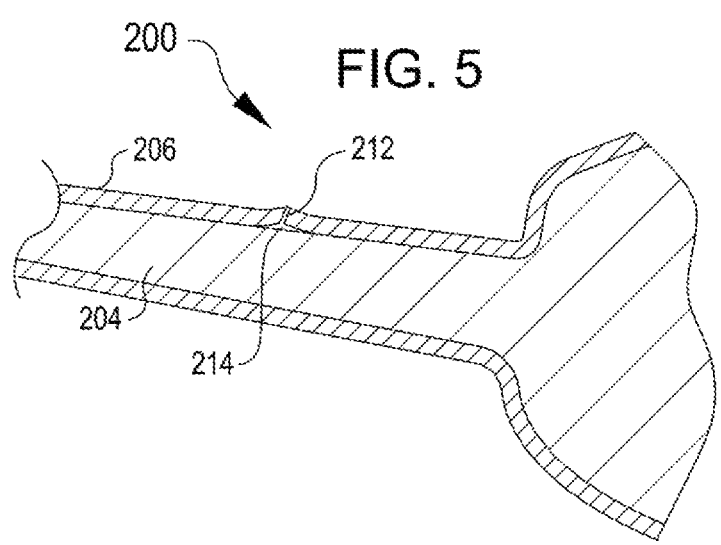
FIG. 5 illustrates the composite structure of FIG. 2, in a diagrammatic side section view, showing a break in a composite skin.

FIG. 5 illustrates the composite structure 200 of FIG. 2, in a diagrammatic side section view, showing a break 212 in a composite skin forming the outer layer 206. The break 212 alone can disrupt thermal transfer in the outer layer 206. If the break 212 penetrates the outer layer 206 it can form a void 214 between the outer layer and the substrate 204 which can disrupt thermal transfer between the substrate and outer layer.

Figure 6:
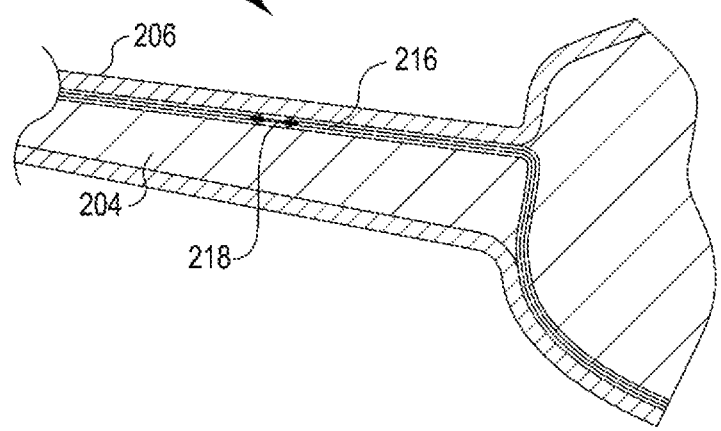
FIG. 6 illustrates the composite structure of FIG. 2, in a diagrammatic side section view, showing a break in an internal component under the composite skin.

FIG. 6 illustrates the composite structure 200 of FIG. 2, in a diagrammatic side section view, showing a break 218 in an internal component 218 under the composite skin forming the outer layer 206. Various components and substructures may be present in a composite structure, such as power cables, circuits, structural elements, and the like. Any component or substructure which contacts the outer layer 206 may contribute to thermal transfer to and from the outer layer. Thus, a discontinuity such as the break 218 in the internal component 216 may be visible by way of thermographic methods due to the disruption to thermal transfer from the outer layer 206.

Various other forms of manufacturing defect or damage may be detected by methods herein described. For example, another common incident in manufacturing composite parts is the accidental inclusion of a foreign object, such as a tool or debris, between an outer skin and substrate, or between layers of a multi-ply composite skin. Such foreign objects generally disrupt transfer of heat through the composite skin even when thin enough to avoid manual detection, and thus may be readily visible by thermographic methods.

Figure 7:
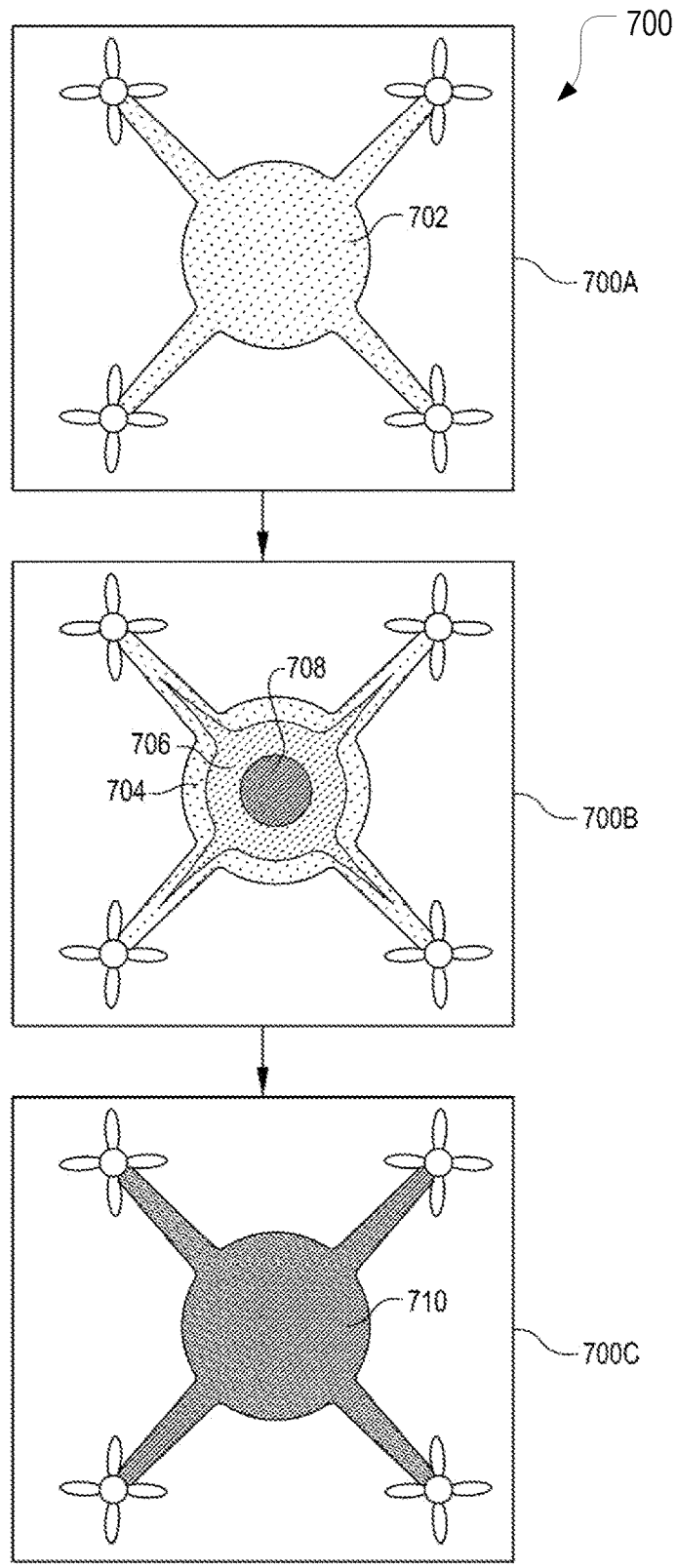
FIG. 7 illustrates an example of thermographic data visualized as thermographic images of a composite structure.

FIG. 7 illustrates an example of temperature data 700 visualized as thermographic images 700A-C of a composite structure similar to the composite structure 102 shown in FIG. 1. The temperature data 700 is broadly illustrative of the information obtained by way of a scanning stage (e.g., scanning stage 110) that obtains temperature data of a structure after a chilling step and subsequent heating step (e.g., chilling stage 106 and heating stage 108, respectively).

The first thermographic image 700A shows temperature data in the form of a temperature map immediately after a heating step. The temperature data may be stored numerically, e.g., as intensity values associated with discrete three-dimensional spatial locations (voxels) or two-dimensional locations in the image (pixels). Immediately after the heating step, the outer surface of a scanned composite structure may have approximately uniform temperature, and can be shown at a substantially uniform first thermal intensity 702.

The second thermographic image 700B shows temperature data in the form of a second temperature map at a predetermined time after a heating step. The second thermographic image may show some degree of patterning caused by non-uniform temperature changes across the outer layer of the composite structure. For example, discreet bands 704, 706, 708 at different temperatures may appear where the thermal conductivity of the outer layer and/or substrate vary, e.g., with outer layer thickness, with different materials underneath the outer layer, or with voids. The temperature data for thermographic methods disclosed herein is preferably obtained during a window in which a temperature difference between the outer layer and the substrate is driving thermal change, as shown in image 700B. For typical composite structures, and for an initial temperature difference of about 33° C. between the first steady-state temperature and the transitory temperature to which the outer layer is heated, the window for obtaining thermographic data is on the order of 30-40 seconds after removal from the heating stage. However, in some cases, the window may be shorter (e.g., for thin outer layers or for substrates with higher thermal conductivity), or longer (e.g., for thick outer layers). Thus, thermographic data may be obtained in different cases as early as 10 seconds after removal from the heating stage.

The third thermographic image 700C shows temperature data in the form of a third temperature map, taken at a relatively long period of time (i.e., order of minutes) after the heating step. Heat applied to the outer surface is quickly transferred away from the outer layer and into the substrate of the composite structure, causing the outer layer of the composite structure to revert to a substantially uniform temperature profile.

Figure 8:
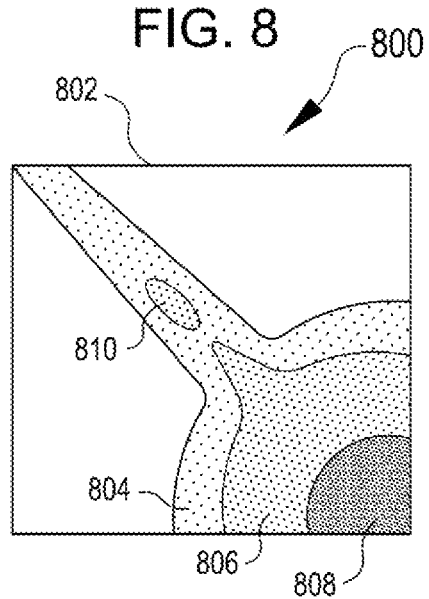
FIG. 8 illustrates an example of a local temperature irregularity in a thermographic image of a portion of a composite structure.

FIG. 8 illustrates an example of a local temperature irregularity 810 in a thermographic image 800 showing temperature data concerning a portion of a composite structure, in accordance with embodiments. After temperature data is obtained from a composite structure coming to thermal equilibrium, i.e., after a heating step, the temperature data can be presented as a thermographic image 800. The thermographic image 800 shows discrete temperature zones 804, 806, 808 that are predictable in shape and intensity. An irregularity 810 can be detected as an unexpected region of higher or lower intensity in the thermographic image 800. Generally, an irregularity such as a disband or delamination, which will reduce the thermal conductivity of the outer layer, will result in the irregularity 810 having a higher intensity (corresponding to a higher temperature) because the heat in the outer layer is taking longer than expected to conduct to the cooler substrate. An irregularity that results in less material in the outer layer, e.g., a hole or divot caused by removal or compression of material, may result in the irregularity 810 having a lower intensity than surrounding material due to the heat in the outer layer passing to the cooler substrate more rapidly.

Figure 9:
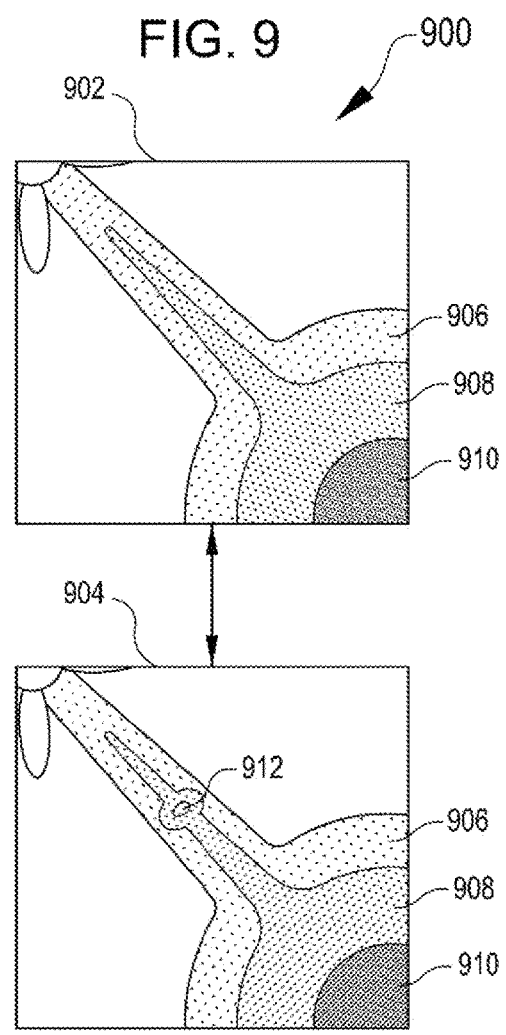
FIG. 9 illustrates an example of a comparison between a reference thermographic image and a thermographic image indicative of an irregularity in the composite structure.

FIG. 9 illustrates an example of a comparison 900 between a reference thermographic image 902 and an obtained thermographic image 904 indicative of an irregularity in the composite structure. The reference thermographic image 902 corresponds to temperature data taken of a representative, or reference, composite structure that is free of defects or irregularities, and demonstrates a clear thermal pattern having predictable temperature zones 906, 908, 910. The obtained thermographic image 904 shows an irregularity 912 in the temperature data, which appears as a deviation from the reference thermographic image 902.

The reference thermographic image 902 and the obtained thermographic image 904 may be obtained from a composite component under similar parameters, and thus may substantially match with respect to the temperature zones 906, 908, 910. However, in some cases, the obtained thermographic image may be mathematically corrected to conform to the reference thermographic image (e.g., by adjusting intensity values to substantially conform the images to one another). In some cases, multiple instances of temperature data may be obtained at intervals, and temperature data may be selected by matching a best fit image of the multiple instances of temperature data to the reference thermographic image.

The temperature data may be obtained in a system similar to the system 100 shown in FIG. 1, but may also be obtained with reference to similar systems as shown with reference to FIGS. 10-13. FIGS. 10-13 illustrate multiple example systems for obtaining thermographic data from a composite structure.

Figure 10:
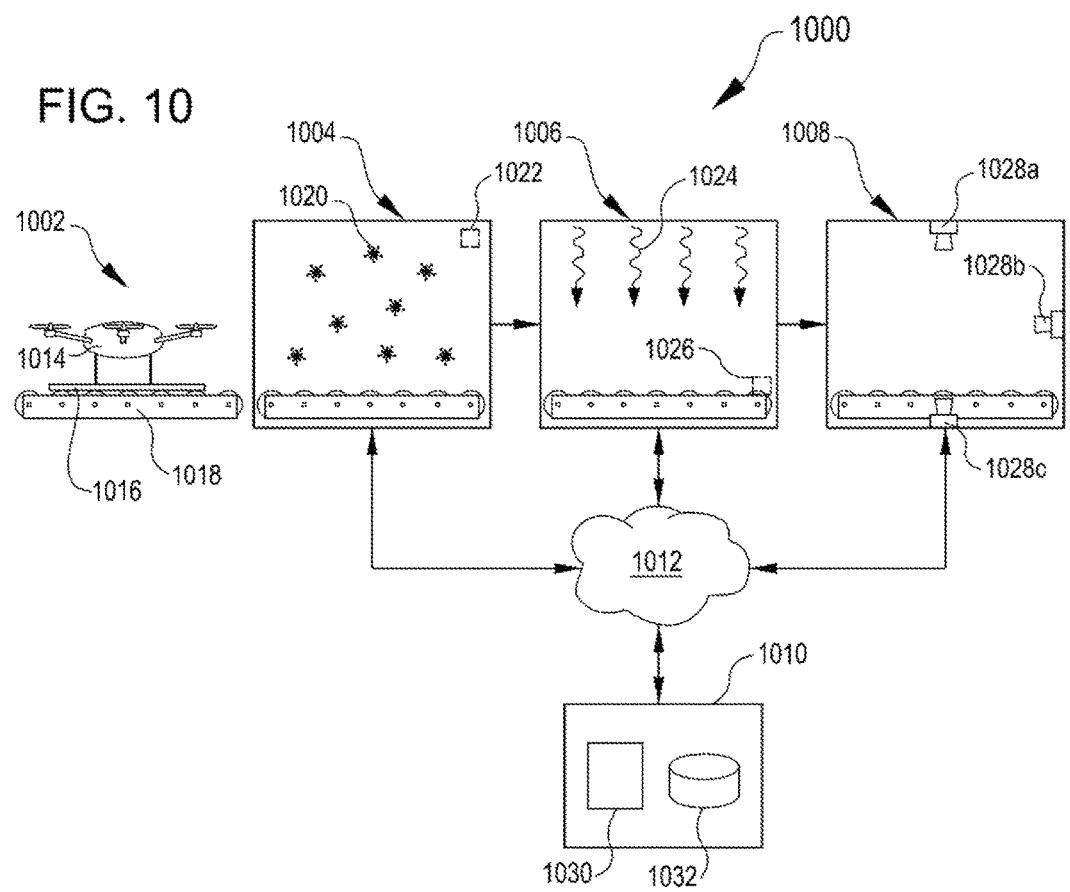
FIG. 10 illustrates an example of a second system for thermographically inspecting a composite structure, in accordance with embodiments.

FIG. 10 illustrates an example of a second system 1000 for thermographically inspecting a composite structure 1002, in accordance with embodiments. In the system 1000, the composite structure 1014 is shown as a UAV, however, it will be understood that the composite structure may be any suitable composite vehicle, equipment, vehicle part, or similar component.

The system 1000 can include a drive module 1018 for moving the composite structure 1002 through the system 1000. The drive module 1018 is shown in the form of a conveyor and platform 1016, which can receive the composite structure 1002 at a receiving stage 1002. The system 1000 includes, in series, a chilling module 1004, a heating module 1006, and a scanning module 1008 which may be controlled by a management component 1010 with processing 1030 and memory 1032. The modules may communicate with and be controlled by the management component 1010 by way of a network 1012.

The composite structure 1014 can be transferred to the chilling module 1004 where it can be retained for a predetermined period of time sufficient to bring the composite structure to a first temperature. The chilling module 1004 can be equipped with a chilling mechanism 1020 for cooling the composite structure 1014. The temperature of the chilling module may be monitored by, e.g., a first temperature sensor 1022. The composite structure 1014 can then be transferred to a heating module 1006, where a heating mechanism 1024 can apply heat to the outer surface of the composite structure 1014. The temperature in the heating module can also be monitored by a second temperature sensor 1026. The heating mechanism 1024 can be any suitable heating mechanism as discussed above with respect to system 100 shown in FIG. 1.

The composite structure 1014 can be transferred to the scanning module 1008 to be scanned by one or more thermographic sensors 1028a, 1028b, 1028c (cumulatively 1028). The thermographic sensors 1028a are operable to obtain temperature data from the composite structure 1014, which may be in the form of one or more infrared images showing thermal radiation from the composite structure 1014. The temperature data from the thermographic sensors 1028 can be processed by the management component 1010.

Figure 11:
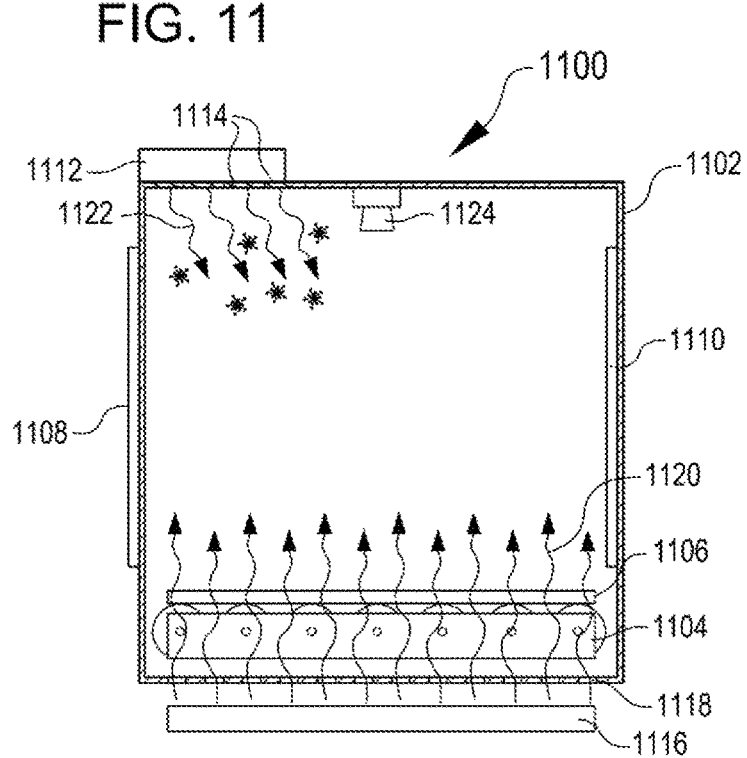
FIG. 11 illustrates an example of a third system for thermographically inspecting a composite structure, in accordance with embodiments.

FIG. 11 illustrates an example of a third example system 1100 for thermographically inspecting a composite structure, in accordance with embodiments. Whereas the system 1000 shown in FIG. 10 illustrated a multi-stage system that can transfer a composite structure therethrough, the system 1100 shown in FIG. 11 illustrates that various components of a thermographic inspection system can be integrated into a single enclosure 1102. For example, the enclosure 1102 can be accessed via one or more entry and/or exit ports 1108, 1110, and can include a drive module 1104 and a platform 1106 for conveying a composite structure therethrough. A chilling module 1112 may be arranged to pass flow of cold air 1122 into the enclosure 1102 in order to chill a composite structure therein, e.g., via cold air vents 1114. A heating module 1116 may be arranged to pass a flow of hot air 1120 via hot air vents 1118 into the enclosure 1102, or to direct heat by infrared radiation. One or more thermographic sensors 1124 may be positioned in the enclosure 1102 to capture temperature data concerning the outer surface of a composite structure within the enclosure. Chilling, heating, and thermal scanning steps common to systems 100 and 1000 (FIGS. 1 and 10) may thus be performed within a common module. In order to achieve rapid changes to the environment in the enclosure 1102, the air within the enclosure may be rapidly purged between steps.

Figure 12:
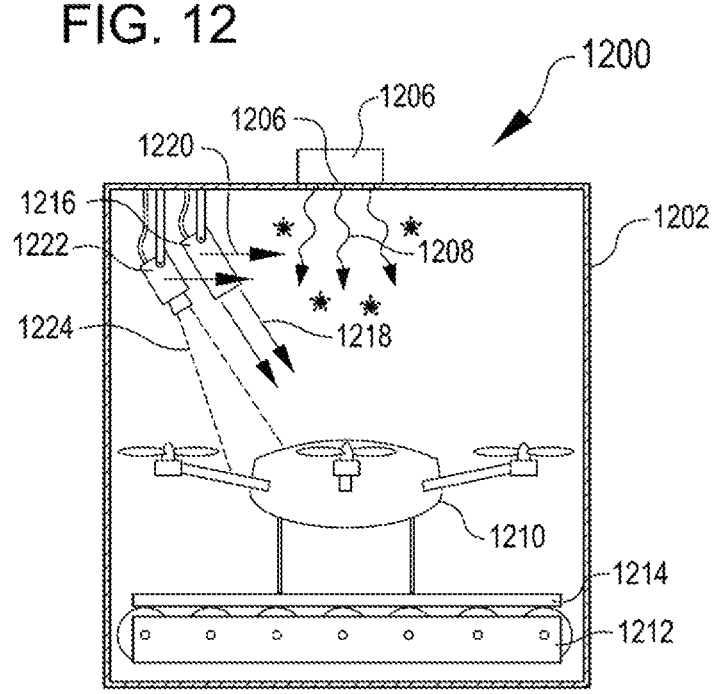
FIG. 12 illustrates an example of a fourth system for thermographically inspecting a composite structure, in accordance with embodiments.

FIG. 12 illustrates an example of a fourth example system 1200 for thermographically inspecting a composite structure 1210, in accordance with embodiments. Similar to the system 1100 discussed with reference to FIG. 11, the system 1200 can include an enclosure 1202, a drive module 1212 and platform 1214 for moving the composite structure 1210 through the system, and a chilling module 1206 which can chill the composite structure to a first steady-state temperature.

FIG. 12 shows an alternative mechanism for heating and scanning the composite structure, in accordance with some embodiments. A heating module 1216 can be arranged to scan across the composite structure 1210, e.g., in a horizontal direction 1216 across the composite structure. The heating module 1216 can be arranged on a track, on a robotic arm, or on a swivel to scan across the composite structure 1210. In some cases, the heating module 1216 may be positioned in a stationary manner while the drive module 1212 moves the composite structure 1210 underneath the heating module. The heating module 1216 can direct heat 1218, e.g., via a flow of hot air, a beam of infrared energy, or the like, in a directed manner to contact and heat the outer layer of the composite structure 1210. In some cases, the heating module 1216 may be a "thermal gun."

A scanning module 1222 can be arranged to scan across the composite structure 1210 at a predetermined distance behind the heating module 1216, or after a predetermined period of time after the heating module scans the composite structure. The scanning module 1222 can include any infrared sensor capable of resolving temperature at the outer layer of the composite structure 1210, e.g., an infrared camera. In some cases, the scanning module 1222 can have a restricted viewing angle 1224; and the temperature data obtained by the scanning module 1222 can be reconstructed by adding multiple sections together to form a thermographic image.

Figure 13:
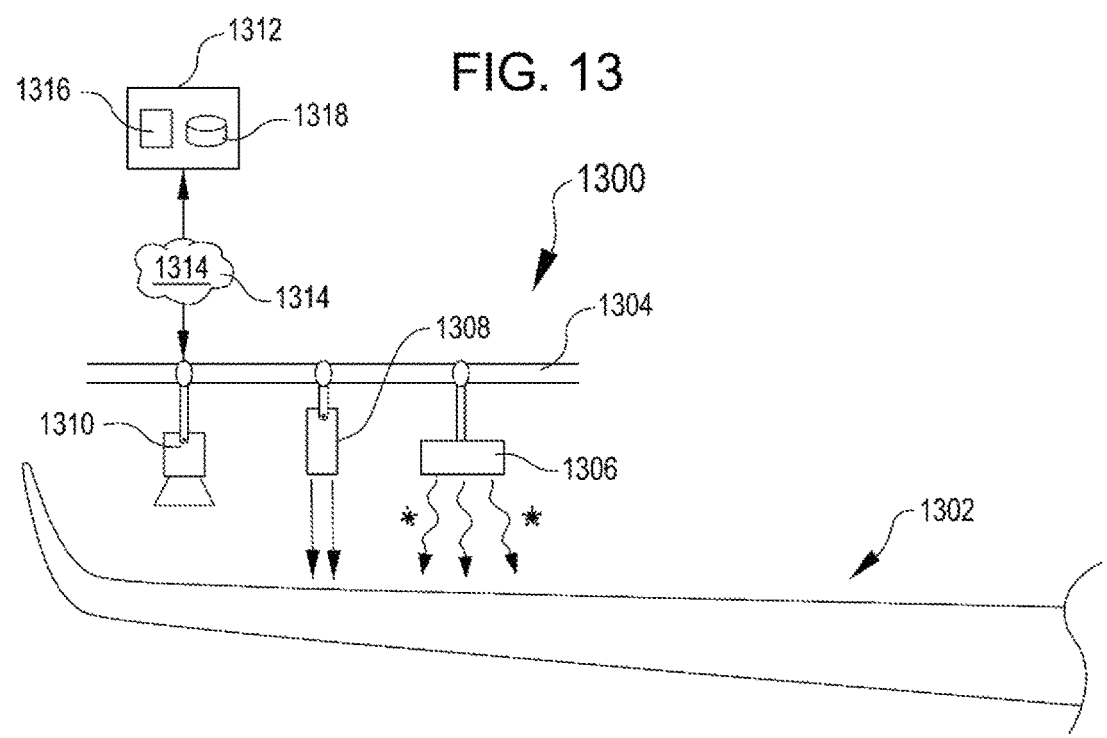
FIG. 13 illustrates an example of a fifth system for thermographically inspecting a composite structure, in accordance with embodiments.

FIG. 13 illustrates an example of a fifth example system 1300 for thermographically inspecting a composite structure 1302, in accordance with embodiments. The system 1300 illustrates how the principles herein disclosed may be applied to obtain thermographic data for a large composite structure or in cases where an environmentally controlled enclosure may be difficult to maintain. A chilling module 1306, a heating module 1308, and a scanning module 1310 may be retained on a support 1304, such as a rail, robotic arm, swivel, or other suitable support structure and suspended a distance from the composite structure 1302. The modules 1306, 1306, 1310 may be controlled by a management component 1312 including processors and memory 1316, 1318, which may communicate with the modules by way of a network 1314.

In some embodiments, the chilling module 1306 may scan across the composite structure 1302 in order to chill the composite structure. The chilling module 1306 is preferably operable to chill the composite structure at least to a depth that includes chilling both an outer layer and a substrate of the composite structure to a steady state temperature. After the composite structure is chilled, the heating module 1308 can scan across the composite structure 1302 to direct heat to the outer layer of the composite structure 1302. In some cases, the heating module 1308 can be arranged to follow the chilling module 1306, such that both modules sweep from one position relative to the composite structure 1302 to a second position. The heating module 1308 can comprise any suitable mechanism for directing heat to a surface, similar to the heating module 1216 described in FIG. 12. After the outer layer is heated, the scanning module 1310 can scan across the composite structure 1302 to obtain temperature data concerning the surface temperatures of the outer layer of the composite structure. The scanning module 1310 can follow a predetermined distance behind the heating module, or after a predetermined length of time has elapsed after the outer layer is heated. The temperature data obtained by the scanning module can be used to construct a thermographic image of the composite structure, which may be used for identifying irregularities therein.

Figure 14:
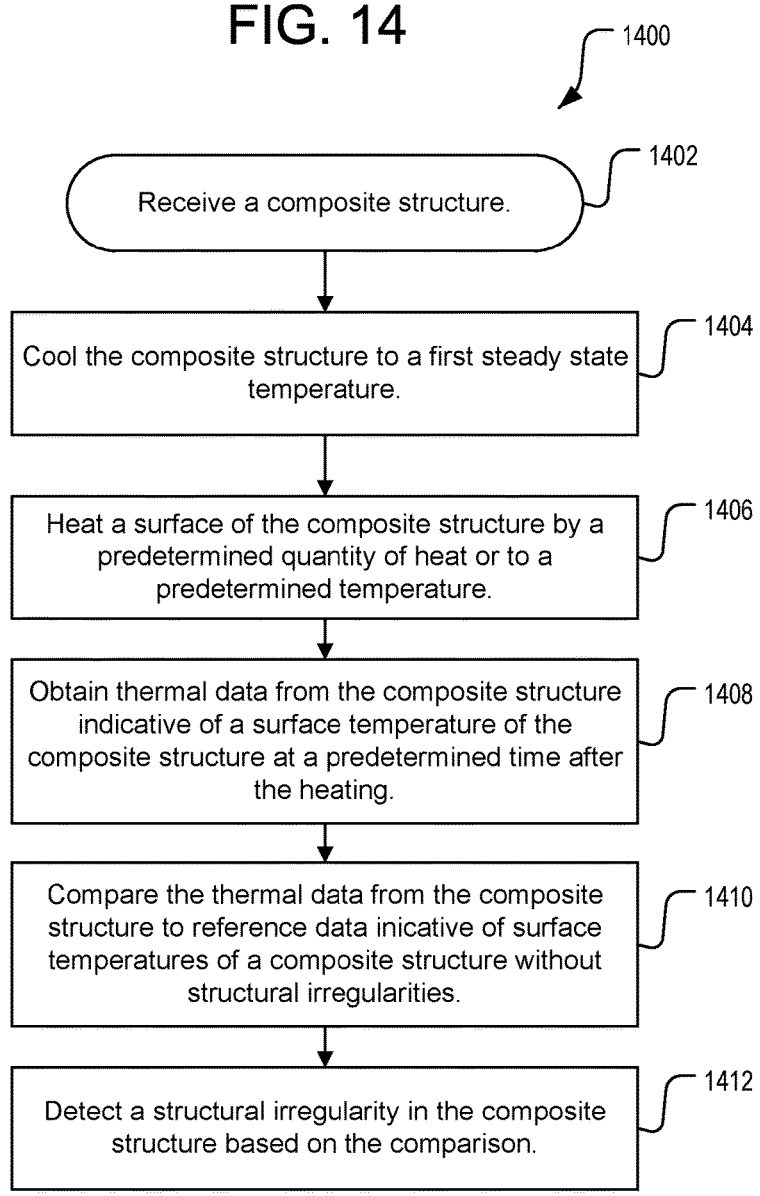
FIG. 14 illustrates a first example process for thermographically inspecting a composite structure.
Figure 15:
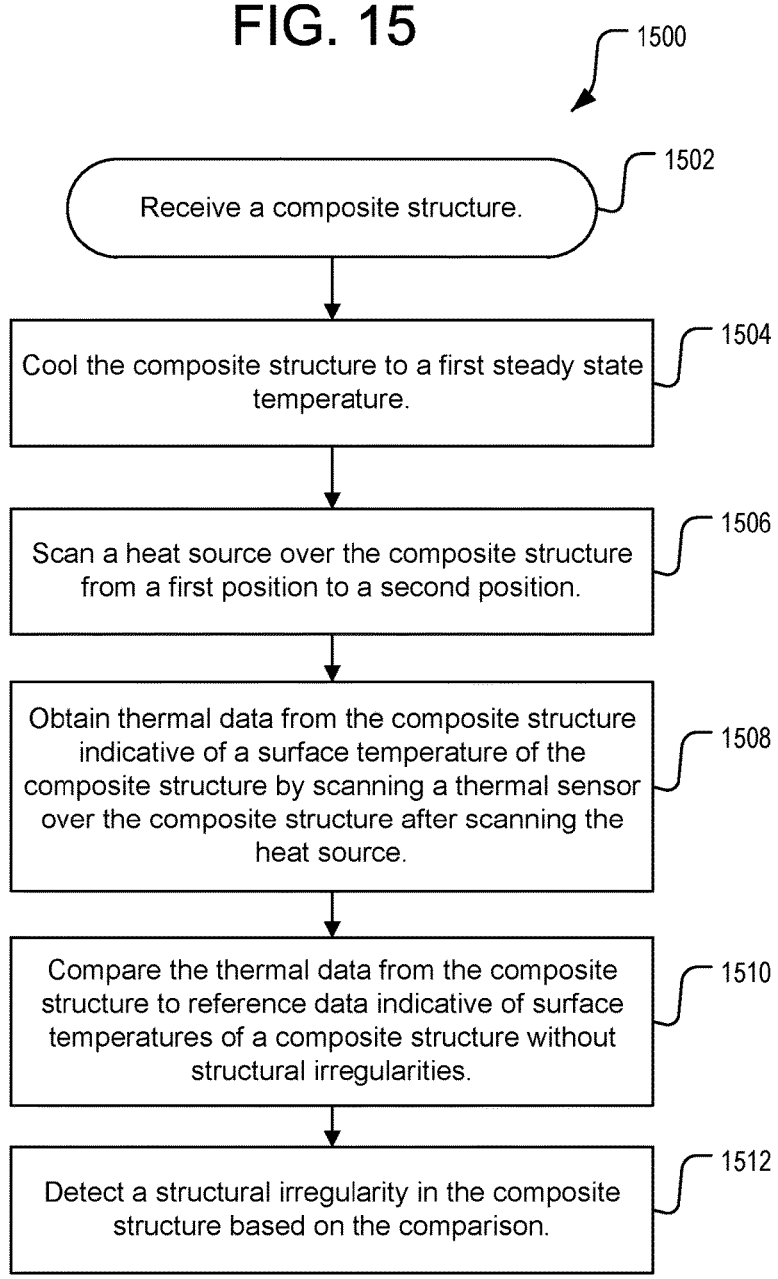
FIG. 15 illustrates a second example process for thermographically inspecting a composite structure.
Figure 16:
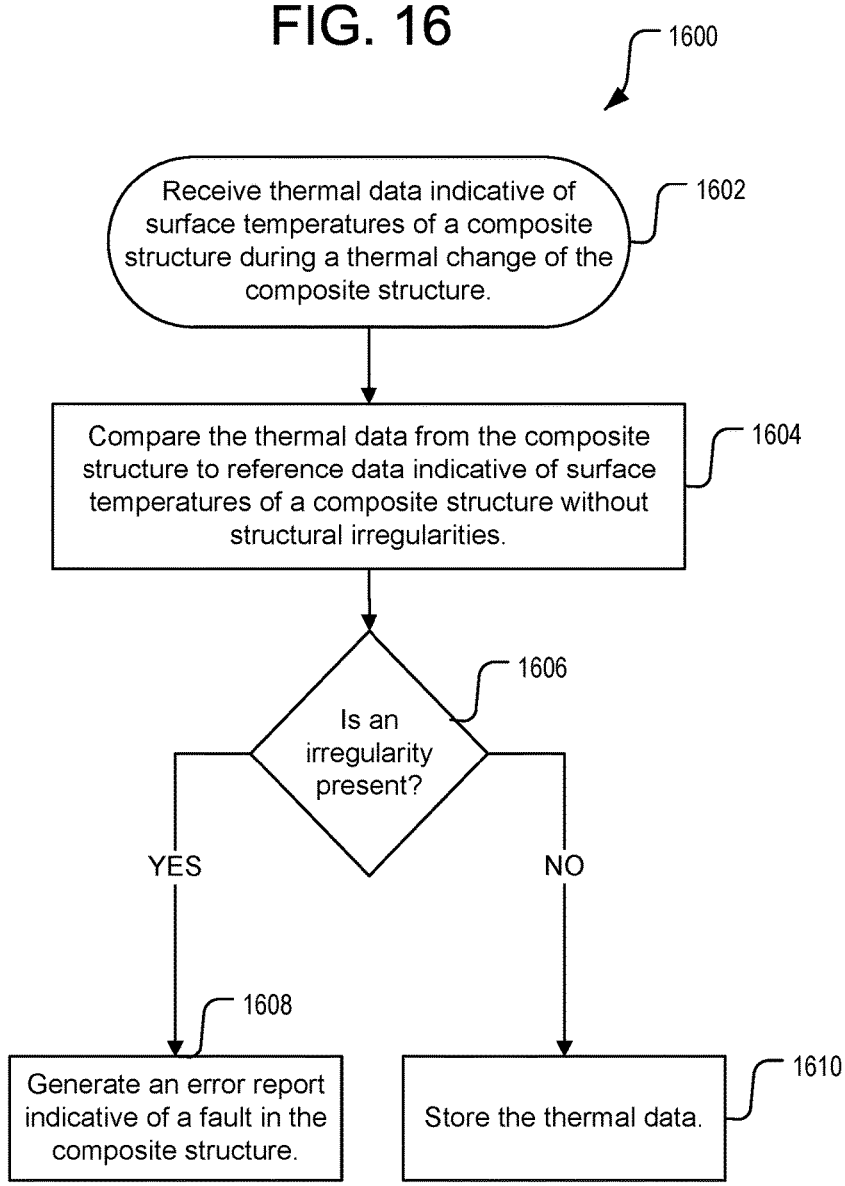
FIG. 16 illustrates a third example process for thermographically inspecting a composite structure.

FIGS. 14-16 illustrate example processes for thermographically inspecting a composite structure or a composite vehicle. Some or all of the processes 1400, 1500, or 1600 (or any other processes described herein, or variations, and/or combinations thereof) may be performed under the control of one or more computer systems configured with executable instructions and may be implemented as code (e.g., executable instructions, one or more computer programs, or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

FIG. 14 illustrates a first example process 1400 for thermographically inspecting a composite structure, in accordance with embodiments. Aspects of the process 1400 can be performed, in some embodiments, by a system similar to the system 100 discussed in FIG. 1, the system 1000 discussed in FIG. 10, or the system 1100 discussed in FIG. 11. The system may be implemented with respect to any suitable composite structure, such as a composite UAV, or a composite structure of a larger vehicle such as a component of a composite automotive or airframe component, composite sporting equipment, or similar component.

In an embodiment, the process 1400 includes receiving a composite structure, e.g., at a staging position or in an enclosure operable to induce a temperature change in the structure (act 1402). The composite structure is cooled to a first steady-state temperature (act 1404). Then, the composite structure is subjected to surface heating by a heat source (act 1406). After a predetermined period of time, or after an outer layer of the composite structure has reached a predetermined temperature, the system obtains temperature data from the composite structure that indicates temperatures over the outer layer of the structure (act 1408). The temperature data may be in the form of a thermographic image. The temperature data can be compared to reference data, e.g., a reference thermographic image obtained from an undamaged composite structure of the same type as the composite structure, or reference data obtained previously from thermal scanning of the same composite structure (act 1410). The comparison can highlight changes in thermal conductivity of the composite structure compared to the reference structure, indicative of an irregularity in the composite structure (act 1412).

FIG. 15 illustrates a second example process 1500 for thermographically inspecting a composite structure. Aspects of the process 1500 can be performed, in some embodiments, by a system similar to the system 100 discussed in FIG. 1, the system 1000 discussed in FIG. 10, or the system 1100 discussed in FIG. 11. The system may be implemented with respect to any suitable composite structure, such as a composite UAV, or a composite structure of a larger vehicle such as a component of a composite automotive or airframe component, composite sporting equipment, or similar component.

In an embodiment, the process 1500 can also include receiving a composite structure, e.g., at a staging position or in an enclosure operable to induce a temperature change in the structure (act 1502). The composite structure is cooled to a first steady-state temperature (act 1504). Then, the composite structure is subjected to surface heating by a heat source that scans over a surface of the composite structure (act 1506). A suitable heat source can include a "thermal knife," e.g., a blower pushing hot air in a narrow band or sheet, or an infrared emitter that provides thermal emissions over a discrete band. After a predetermined period of time, or at a predetermined distance behind the heat source, the system can obtains temperature data from the composite structure that indicates temperatures over the outer layer of the structure by, e.g., scanning the composite structure with a thermographic sensor (act 1508). The temperature data may be converted into the form of a thermographic image, and may be compared to reference data, e.g., a reference thermographic image obtained from an undamaged composite structure of the same type as the composite structure, or reference data obtained previously from thermal scanning of the same composite structure (act 1510). The comparison can highlight changes in thermal conductivity of the composite structure compared to the reference structure, indicative of an irregularity in the composite structure (act 1510).

FIG. 16 illustrates a third example process 1600 for thermographically inspecting a composite structure. Aspects of the process 1600 can be performed, in some embodiments, by a system similar to the system 100 discussed in FIG. 1, the system 1000 discussed in FIG. 10, or the system 1100 discussed in FIG. 11. The system may be implemented with respect to any suitable composite structure, such as a composite UAV, or a composite structure of a larger vehicle such as a component of a composite automotive or airframe component, composite sporting equipment, or similar component.

In an embodiment, the process 1600 can also include receiving temperature data indicative of surface temperatures of a composite structure during a thermal change of the composite structure (act 1602). The temperature data may in a numerical form, in the form of a thermographic image, or in any other suitable form. The temperature data may be converted into the form of a thermographic image. The temperature data may be compared to reference data, e.g., a reference thermographic image obtained from an undamaged composite structure of the same type as the composite structure, reference data obtained previously from thermal scanning of the same composite structure (act 1604). In some cases, temperature data may be compared to other attributes of the same temperature data set. For example, an average or median value may be obtained from the temperature data and set as a reference value; or a reference value may be predefined. The temperature data corresponding to each region (e.g., pixels or sets of pixels of a thermographic image) can be compared against the reference value and used to determine whether an irregularity is present at each region (act 1606). If an irregularity is present, the system can generate an error report indicating the irregularity, and may provide an indication for presentation to a user to alert the user of the irregularity (act 1608). The indication may include coordinates of the irregularity. If an irregularity is not present, the system can log the temperature data for future use, e.g., as reference data, or for maintaining an inspection record (act 1610).

Figure 17:
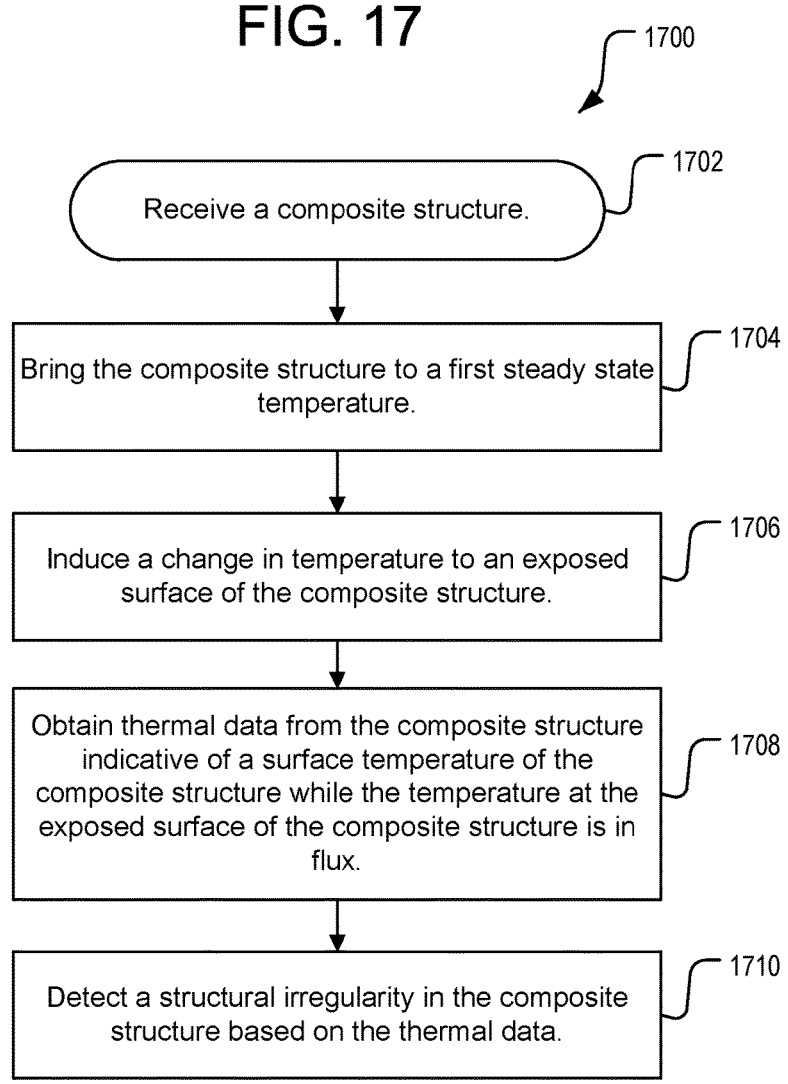
FIG. 17 illustrates a fourth example process for thermographically inspecting a composite structure.

FIG. 17 illustrates a fourth example process 1700 for thermographically inspecting a composite structure. Aspects of the process 1700 can be performed, in some embodiments, by a system similar to the system 100 discussed in FIG. 1, the system 1000 discussed in FIG. 10, or the system 1100 discussed in FIG. 11. The system may be implemented with respect to any suitable composite structure, such as a composite UAV, or a composite structure of a larger vehicle such as a component of a composite automotive or airframe component, composite sporting equipment, or similar component. Suitable systems for performing the process 1700 may differ from systems such as the systems 100, 1000, 1100 (FIGS. 1, 10, 11) by having heating and cooling mechanisms positioned in an inverted order, e.g., with heating mechanisms positioned for use prior to cooling mechanisms.

In an embodiment, the process 1700 can include receiving a composite structure (act 1702), e.g., at a staging position of a system or in an enclosure operable to induce a temperature change in the structure, or in position to have heating and/or cooling mechanisms applied to induce temperature changes in the structure. The composite structure can be brought to a first steady-state temperature by the system, which may include applying heat until the composite structure is at substantially the same temperature throughout, which may be higher than an ambient temperature (act 1704). The system can induce a temperature change at an exposed surface of the composite structure (act 1706). In some cases, inducing the temperature change can involve subjecting a heated composite structure to a flux of cold air, or to a chamber enclosing an amount of cold air. In some other cases, inducing the temperature change can involve subjecting a heated composite structure to a cold flow of a different cooling fluid than air, e.g., a brief spray or submersion in a cooling liquid. Generally, the temperature change involves a transitory temperature change by a predetermined delta. In some cases, the delta can range from about 11° C. to about 33° C., or more. After a predetermined period of time, the system can obtains temperature data from the composite structure by, e.g., scanning the composite structure with a thermographic sensor (act 1708). The thermal data can be used to detect changes is thermal conductivity of the composite structure that correspond to irregularities in the composite structure, according to similar methods to those described above with reference to FIGS. 14-16 (act 1710).

Figure 18:
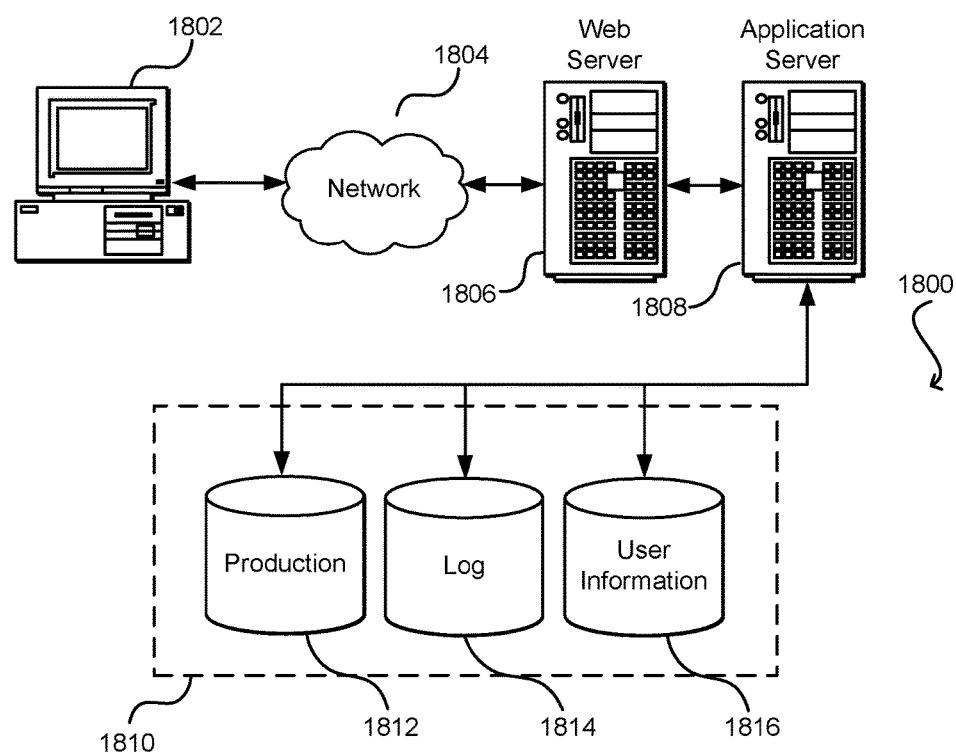
FIG. 18 illustrates an environment in which various embodiments can be implemented.

FIG. 18 illustrates aspects of an example environment 1800 for implementing aspects in accordance with various embodiments. As will be appreciated, although a Web-based environment is used for purposes of explanation, different environments may be used, as appropriate, to implement various embodiments. The environment includes an electronic client device 1802, which can include any appropriate device operable to send and receive requests, messages, or information over an appropriate network 1804 and convey information back to a user of the device. Examples of such client devices include personal computers, cell phones, handheld messaging devices, laptop computers, set-top boxes, personal data assistants, electronic book readers, and the like. The network can include any appropriate network, including an intranet, the Internet, a cellular network, a local area network, or any other such network or combination thereof. Components used for such a system can depend at least in part upon the type of network and/or environment selected. Protocols and components for communicating via such a network are well known and will not be discussed herein in detail. Communication over the network can be enabled by wired or wireless connections and combinations thereof. In this example, the network includes the Internet, as the environment includes a Web server 1806 for receiving requests and serving content in response thereto, although for other networks an alternative device serving a similar purpose could be used as would be apparent to one of ordinary skill in the art.

The illustrative environment includes at least one application server 1808 and a data store 1810. It should be understood that there can be several application servers, layers, or other elements, processes, or components, which may be chained or otherwise configured, which can interact to perform tasks such as obtaining data from an appropriate data store. As used herein the term "data store" refers to any device or combination of devices capable of storing, accessing, and retrieving data, which may include any combination and number of data servers, databases, data storage devices, and data storage media, in any standard, distributed, or clustered environment. The application server can include any appropriate hardware and software for integrating with the data store as needed to execute aspects of one or more applications for the client device, handling a majority of the data access and business logic for an application. The application server provides access control services in cooperation with the data store and is able to generate content such as text, graphics, audio, and/or video to be transferred to the user, which may be served to the user by the Web server in the form of HyperText Markup Language ("HTML"), Extensible Markup Language ("XML"), or another appropriate structured language in this example. The handling of all requests and responses, as well as the delivery of content between the client device 1802 and the application server 1808, can be handled by the Web server. It should be understood that the Web and application servers are not required and are merely example components, as structured code discussed herein can be executed on any appropriate device or host machine as discussed elsewhere herein.

The data store 1810 can include several separate data tables, databases or other data storage mechanisms and media for storing data relating to a particular aspect. For example, the data store illustrated includes mechanisms for storing production data 1812 and user information 1816, which can be used to serve content for the production side. The data store also is shown to include a mechanism for storing log data 1814, which can be used for reporting, analysis, or other such purposes. It should be understood that there can be many other aspects that may need to be stored in the data store, such as for page image information and to access right information, which can be stored in any of the above listed mechanisms as appropriate or in additional mechanisms in the data store 1810. The data store 1810 is operable, through logic associated therewith, to receive instructions from the application server 1808 and obtain, update or otherwise process data in response thereto. In one example, a user might submit a search request for a certain type of item. In this case, the data store might access the user information to verify the identity of the user and can access the catalog detail information to obtain information about items of that type. The information then can be returned to the user, such as in a results listing on a Web page that the user is able to view via a browser on the user device 1802. Information for a particular item of interest can be viewed in a dedicated page or window of the browser.

Each server typically will include an operating system that provides executable program instructions for the general administration and operation of that server and typically will include a computer-readable storage medium (e.g., a hard disk, random access memory, read only memory, etc.) storing instructions that, when executed by a processor of the server, allow the server to perform its intended functions. Suitable implementations for the operating system and general functionality of the servers are known or commercially available and are readily implemented by persons having ordinary skill in the art, particularly in light of the disclosure herein.

The environment in one embodiment is a distributed computing environment utilizing several computer systems and components that are interconnected via communication links, using one or more computer networks or direct connections. However, it will be appreciated by those of ordinary skill in the art that such a system could operate equally well in a system having fewer or a greater number of components than are illustrated in FIG. 18. Thus, the depiction of the system 1800 in FIG. 18 should be taken as being illustrative in nature and not limiting to the scope of the disclosure.

The various embodiments further can be implemented in a wide variety of operating environments, which in some cases can include one or more user computers, computing devices or processing devices which can be used to operate any of a number of applications. User or client devices can include any of a number of general purpose personal computers, such as desktop or laptop computers running a standard operating system, as well as cellular, wireless, and handheld devices running mobile software and capable of supporting a number of networking and messaging protocols. Such a system also can include a number of workstations running any of a variety of commercially-available operating systems and other known applications for purposes such as development and database management. These devices also can include other electronic devices, such as dummy terminals, thin-clients, gaming systems, and other devices capable of communicating via a network.

Most embodiments utilize at least one network that would be familiar to those skilled in the art for supporting communications using any of a variety of commercially-available protocols, such as Transmission Control Protocol/Internet Protocol ("TCP/IP"), Open System Interconnection ("OSI"), File Transfer Protocol ("FTP"), Universal Plug and Play ("UpnP"), Network File System ("NFS"), Common Internet File System ("CIFS"), and AppleTalk®. The network can be, for example, a local area network, a wide-area network, a virtual private network, the Internet, an intranet, an extranet, a public switched telephone network, an infrared network, a wireless network, and any combination thereof.

In embodiments utilizing a Web server, the Web server can run any of a variety of server or mid-tier applications, including Hypertext Transfer Protocol ("HTTP") servers, FTP servers, Common Gateway Interface ("CGI") servers, data servers, Java servers, and business application servers. The server(s) also may be capable of executing programs or scripts in response to requests from user devices, such as by executing one or more Web applications that may be implemented as one or more scripts or programs written in any programming language, such as Java®, C, C#, or C++, or any scripting language, such as Perl, Python, or TCL, as well as combinations thereof. The server(s) may also include database servers, including without limitation those commercially available from Oracle®, Microsoft®, Sybase®, and IBM®.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers, or other network devices may be stored locally and/or remotely, as appropriate. Where a system includes computerized devices, each such device can include hardware elements that may be electrically coupled via a bus, the elements including, for example, at least one central processing unit ("CPU"), at least one input device (e.g., a mouse, keyboard, controller, touch screen, or keypad), and at least one output device (e.g., a display device, printer, or speaker). Such a system may also include one or more storage devices, such as disk drives, optical storage devices, and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired)), an infrared communication device, etc.), and working memory as described above. The computer-readable storage media reader can be connected with, or configured to receive, a computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or Web browser. It should be appreciated that alternate embodiments may have numerous variations from that described above. For example, customized hardware might also be used and/or particular elements might be implemented in hardware, software (including portable software, such as applets), or both. Further, connection to other computing devices such as network input/output devices may be employed.

Storage media computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, Electrically Erasable Programmable Read-Only Memory ("EEPROM"), flash memory or other memory technology, Compact Disc Read-Only Memory ("CD-ROM"), digital versatile disk (DVD), or other optical storage, magnetic cassettes, magnetic tape, magnetic disk storage, or other magnetic storage devices, or any other medium which can be used to store the desired information and which can be accessed by a system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the disclosure as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the disclosure to the specific form or forms disclosed, but on the contrary, the intention is to cover all modifications, alternative constructions, and equivalents falling within the spirit and scope of the disclosure, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the disclosure and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is intended to be understood within the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Preferred embodiments of this disclosure are described herein, including the best mode known to the inventors for carrying out the disclosure. Variations of those preferred embodiments may become apparent to those of ordinary skill in the art upon reading the foregoing description. The inventors expect skilled artisans to employ such variations as appropriate and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A method to detect irregularities in a composite structure, the method comprising:
    cooling the composite structure to a first temperature state;
    applying a quantity of heat to an exposed surface of the composite structure;
    after heat has been applied to the exposed surface of the composite structure, generating temperature data for the exposed surface of the composite structure; and
    detecting an irregularity in the composite structure based on the temperature data.

2. The method of claim 1, further comprising raising a temperature of the exposed surface of the composite structure to at least 43° C. by applying the quantity of heat.

3. The method of claim 1, wherein applying the quantity of heat comprises raising a temperature of the exposed surface of the composite structure to a second temperature state that is greater than the first temperature state by at least 11° C.

4. The method of claim 1, wherein detecting the irregularity comprises detecting a high-intensity region on the structure based on the temperature data that is indicative of a local temperature that is higher than surrounding temperatures in the composite structure.

5. The method of claim 1, further comprising:
    comparing the temperature data to reference temperature data that corresponds to a reference composite structure; and
    wherein detecting the irregularity comprises detecting a high-intensity region on the structure based on the thermographic data that is indicative of a local temperature that is higher than a corresponding reference local temperature of the reference temperature data.

6. The method of claim 1, wherein the composite structure comprises a composite vehicle component having a composite skin attached to a core.

7. The method of claim 1, wherein applying the quantity of heat to the exposed surface of the composite structure comprises directing an infrared heat source toward the composite structure.

8. The method of claim 1, wherein applying the quantity of heat to the exposed surface of the composite structure comprises transferring heat to the composite structure via a convective flow of heated air.

9. The method of claim 1, wherein generating the temperature data from the composite structure comprises capturing a thermographic image via an infrared sensor.

10. A computer-implemented method, comprising:
generating temperature data for a composite structure that is undergoing a thermal change, the temperature data being indicative of surface temperatures of the composite structure, and the thermal change corresponding to an outer layer of the composite structure losing heat to a substrate within the composite structure; and
detecting an irregularity in the composite structure based on the temperature data by detecting an anomalous temperature at an exposed surface of the outer layer, the irregularity corresponding to a damaged portion and/or a manufacturing defect of the composite structure.

11. The computer-implemented method of claim 10, wherein:
the thermal change is driven by a difference between a first temperature of the composite structure and a second temperature of the composite structure, the second temperature being higher than the first temperature.

12. The computer-implemented method of claim 11, wherein:
the thermal change is driven by an initial temperature difference between the first temperature and the second temperature of at least 11° C.

13. The computer-implemented method of claim 10, further comprising:
receiving reference temperature data indicative of surface temperatures of a reference composite structure;
comparing the temperature data to the reference temperature data; and
detecting the irregularity based on determining, by the comparing, that the temperature data contains the anomalous temperature at the exposed surface of the outer layer, the anomalous temperature not being indicated by the reference temperature data.

14. The computer-implemented method of claim 10, wherein the irregularity is one of a void, air bubble, delamination, manufacturing defect, foreign object, or crack in a skin of the outer layer or between the skin and a core of the composite structure.

15. The computer-implemented method of claim 10, further comprising:
storing the temperature data in a database;
comparing the temperature data with previously stored temperature data; and
detecting the irregularity based on determining, by the comparing, that the temperature data contains the anomalous temperature at the exposed surface of the outer layer, the anomalous temperature not being indicated by the previously stored temperature data.

16. A system to detect irregularities in a composite structure, the system comprising:
a chilling mechanism operable to cool a composite structure;
a heating mechanism operable to direct heat to an exposed surface of the composite structure;
a sensor operable to generate temperature data for the exposed surface of the composite structure; and
a management component comprising a processor and memory containing instructions, the instructions executable by the processor to cause the management component to:
cause the chilling mechanism to cool the composite structure to a first temperature state;
after the composite structure has been cooled to the first temperature state, cause the heating mechanism to apply a quantity of heat to the exposed surface of the composite structure;
after heat has been applied to the exposed surface of the composite structure, cause the thermographic sensor to generate the temperature data for the exposed surface of the composite structure; and
process the temperature data to determine whether the composite structure includes an irregularity, the irregularity being indicative of damage and/or a manufacturing defect.

17. The system of claim 16, wherein the management component is further configured to:
generate a temperature map from the temperature data; and
determine that the composite structure includes an irregularity based in part on detecting a high intensity region on the temperature map.

18. The system of claim 17, wherein the management component is further configured to:
receive a reference image, the reference image corresponding to temperature data of a composite structure that does not have damage or defects;
compare the reference image with the temperature map; and
determine that the composite structure includes an irregularity based in part on detecting a high intensity region on the temperature map that is not included in the reference image.

19. The system of claim 17, wherein determining that the composite structure includes an irregularity comprises determining that a temperature at a spatial location of the temperature map is outside a predetermined threshold associated with the spatial location.

20. The system of claim 17, wherein detecting the defect comprises:
determining a mean intensity of the thermographic image; and
determining that an intensity at a spatial location in the thermographic image is greater than the mean intensity by a predetermined threshold.

* * * * *